United States Patent
Kristiansson et al.

(10) Patent No.: US 7,560,714 B2
(45) Date of Patent: Jul. 14, 2009

(54) SENSOR AND SYSTEM FOR SENSING AN ELECTRON BEAM

(75) Inventors: Anders Kristiansson, Lund (SE); Lars Åke Näslund, Furulund (SE); Hans Hallstadius, Lund (SE)

(73) Assignee: Tetra Laval Holdings & Finance S.A., Pully (CH)

( * ) Notice: Subject to any disclaimer, the term of this patent is extended or adjusted under 35 U.S.C. 154(b) by 349 days.

(21) Appl. No.: 11/542,232

(22) Filed: Oct. 4, 2006

(65) Prior Publication Data
US 2007/0114433 A1    May 24, 2007

Related U.S. Application Data

(60) Provisional application No. 60/796,933, filed on May 3, 2006.

(30) Foreign Application Priority Data
Oct. 26, 2005    (SE) ................................. 0502384

(51) Int. Cl.
G01T 1/29     (2006.01)
B65B 55/08    (2006.01)
G01R 19/00    (2006.01)
G01T 1/16     (2006.01)

(52) U.S. Cl. .................................. 250/492.3; 250/397

(58) Field of Classification Search .............. 250/492.3, 250/397
See application file for complete search history.

(56) References Cited

U.S. PATENT DOCUMENTS

| | | | |
|---|---|---|---|
| 2,616,053 A | 10/1952 | Holloway | |
| 5,254,911 A * | 10/1993 | Avnery et al. | 315/366 |
| 5,835,561 A | 11/1998 | Moorman et al. | |
| 6,429,444 B1 | 8/2002 | Korenev et al. | |
| 6,657,212 B2 | 12/2003 | Komori et al. | |
| 2002/0040968 A1 | 4/2002 | Black et al. | |
| 2004/0119024 A1 | 6/2004 | Avnery | |

FOREIGN PATENT DOCUMENTS

JP    2003-153985 A    5/2003

(Continued)

OTHER PUBLICATIONS

U.S. Appl. No. 11/258,212, Kristiansson et al., filed Oct. 26, 2005.

(Continued)

*Primary Examiner*—Jack I Berman
(74) *Attorney, Agent, or Firm*—Buchanan Ingersoll & Rooney PC

(57) ABSTRACT

The present invention refers to a sensor (10) for sensing an intensity of an electron beam generated by an electron beam generator along a path, the electron beam being exited from the generator through an exit window (24). The invention is characterized in that the sensor (10) comprises a conductor (26) located within the path and exposed to the exit window (24), and an insulating housing (28) for shielding the conductor (26), said housing (28) being engaged with the exit window (24) forming a chamber (30) with said exit window (24), and that the conductor (26) is positioned within said chamber (30). The invention also refers to a system for sensing an intensity of an electron beam.

20 Claims, 4 Drawing Sheets

FOREIGN PATENT DOCUMENTS

| | | | |
|---|---|---|---|
| WO | 2004/061890 | A2 | 7/2004 |
| WO | 2004/110868 | A1 | 12/2004 |
| WO | 2004/110869 | A1 | 12/2004 |
| WO | 2005-002973 | A1 | 1/2005 |

OTHER PUBLICATIONS

U.S. Appl. No. 11/258,215, Kristiansson et al., filed Oct. 26, 2005.
International Search Report dated Oct. 26, 2005.

* cited by examiner

SENSOR AND SYSTEM FOR SENSING AN ELECTRON BEAM

THE FIELD OF INVENTION

The present invention refers to a sensor and a system for sensing an electron beam.

PRIOR ART

Within the food packaging industry it has for a long time been used packages formed from a web or a blank of packaging material comprising different layers of paper or board, liquid barriers of for example polymers and gas barriers of for example thin films of aluminium. To extend the shelf-life of the products being packed it is prior known to sterilise the web before the forming and filling operations, and to sterilize the partly formed packages (ready-to-fill packages, RTF packages) before the filling operation. Depending on how long shelf-life is desired and whether the distribution and storage is made in chilled or ambient temperature, different levels of sterilization can be choosen. One way of sterilising a web is chemical sterilization using for example a bath of hydrogen peroxide. Similarly, a ready-to-fill package can be sterilized by hydrogen peroxide, preferably in gas phase.

Another way to sterilize packaging material is to irradiate it by means of electrons emitted from an electron beam emitting device, such as for example an electron beam generator. Such sterilization of a web of packaging material is disclosed in for example the international patent publications WO 2004/110868 and WO 2004/110869. Similar irradiation of ready-to-fill packages is disclosed in the international patent publication WO 2005/002973. The above publications are hereby incorporated by reference.

To provide on-line control of the intensity of the electron beam, and to monitor uniformity variations, electron sensors are used for dose irradiation measurement. A signal from the sensor is analyzed and fed back into an electron beam control system as a feedback control signal. In the sterilization of packaging material, such sensor feedback can be used to assure a sufficient level of sterilization.

One kind of existing sensors for measuring electron beam intensity, based on direct measuring methods, uses a conductor placed within a vacuum chamber. The vacuum chamber is used to provide isolation from the surrounding environment. Because vacuum-based sensors can be relatively large, they are located at positions outside the direct electron beam path to avoid shadowing of target objects. Shadowing can, for example, preclude proper irradiation (and thus, proper sterilization) of packaging material. Therefore, these sensors rely on secondary information from a periphery of the beam, or information from secondary irradiation, to provide a measurement.

In operation, electrons from the electron beam which have sufficient energy will penetrate a window, such as a titanium (Ti) window of the vacuum chamber and be absorbed by the conductor. The absorbed electrons establish a current in the conductor. The magnitude of this current is a measure of the number of electrons penetrating the window of the vacuum chamber. This current provides a measure of the intensity of the electron beam at the sensor position.

A known electron beam sensor has a vacuum chamber with a protective coating, and an electrode representing a signal wire inside the chamber, is described in published U.S. patent application No. US 2004/0119024. The chamber walls are used to maintain a vacuum volume around the electrode. The vacuum chamber has a window accurately aligned with the electrode to sense the electron beam intensity. The sensor is configured for placement at a location, relative to a moving article being irradiated, opposite the electron beam generator for sensing secondary irradiation.

A similar electron beam sensor is described in the international patent publication WO 2004/061890. In one embodiment of this sensor, the vacuum chamber is removed and the electrode is provided with an insulating layer or film. The insulating layer is provided to avoid influence from electrostatic fields and plasma electrons created by the electron beam from substantially influencing the electrode output.

U.S. Pat. No. 6,657,212 describes an electron beam irradiation processing device wherein an insulating film is provided on a conductor, such as a stainless steel conductor, of a current detection unit placed outside a window of an electron beam tube. A current measuring unit includes a current meter that measures current detected. This patent describes advantages of a ceramic coated detector.

SUMMARY OF THE INVENTION

An object of the invention has been to provide a sensor for sensing an electron beam which sensor is small and reliable. The object is achieved with a sensor for sensing an intensity of an electron beam generated by an electron beam generator along a path towards a target within a target area. The electron beam is exited from the generator through an exit window. The sensor is characterized it that it comprises a conductor and an insulating housing. Further, the conductor is located within the path and exposed to the exit window. The insulating housing is shielding the conductor, and said housing is engaged with the exit window forming a chamber with said exit window. Further, the conductor is positioned within said chamber. In this way a sensor is achieved which can be made very small. With a small sensor shadowing of the target is prevented. Further, the sensor is also very reliable since the conductor is directly exposed to the electron beam and the influence of plasma is prevented by means of the insulating housing. Only a negligible and controlled plasma is present within the chamber.

The sensor is further defined by means of the attached dependent claims 2-11.

The invention also refers to a system for sensing an electron beam, which system comprises the sensor described above. Said system further comprises an electron beam generator adapted to generate an electron beam along a path towards a target in a target area, the electron beam being exited from the generator through an exit window. The sensor is engaged with said exit window to detect and measure the electron beam intensity. The system further comprises a support for supporting the target within the target area.

The system is further defined by means of the attached dependent claims 13-19.

BRIEF DESCRIPTION OF THE DRAWINGS

In the following, a presently preferred embodiment of the invention will be described in greater detail, with reference to the enclosed drawings, wherein like reference numerals have been used to designate like elements, in which.

DESCRIPTION OF PREFERRED EMBODIMENTS

Figure 1:
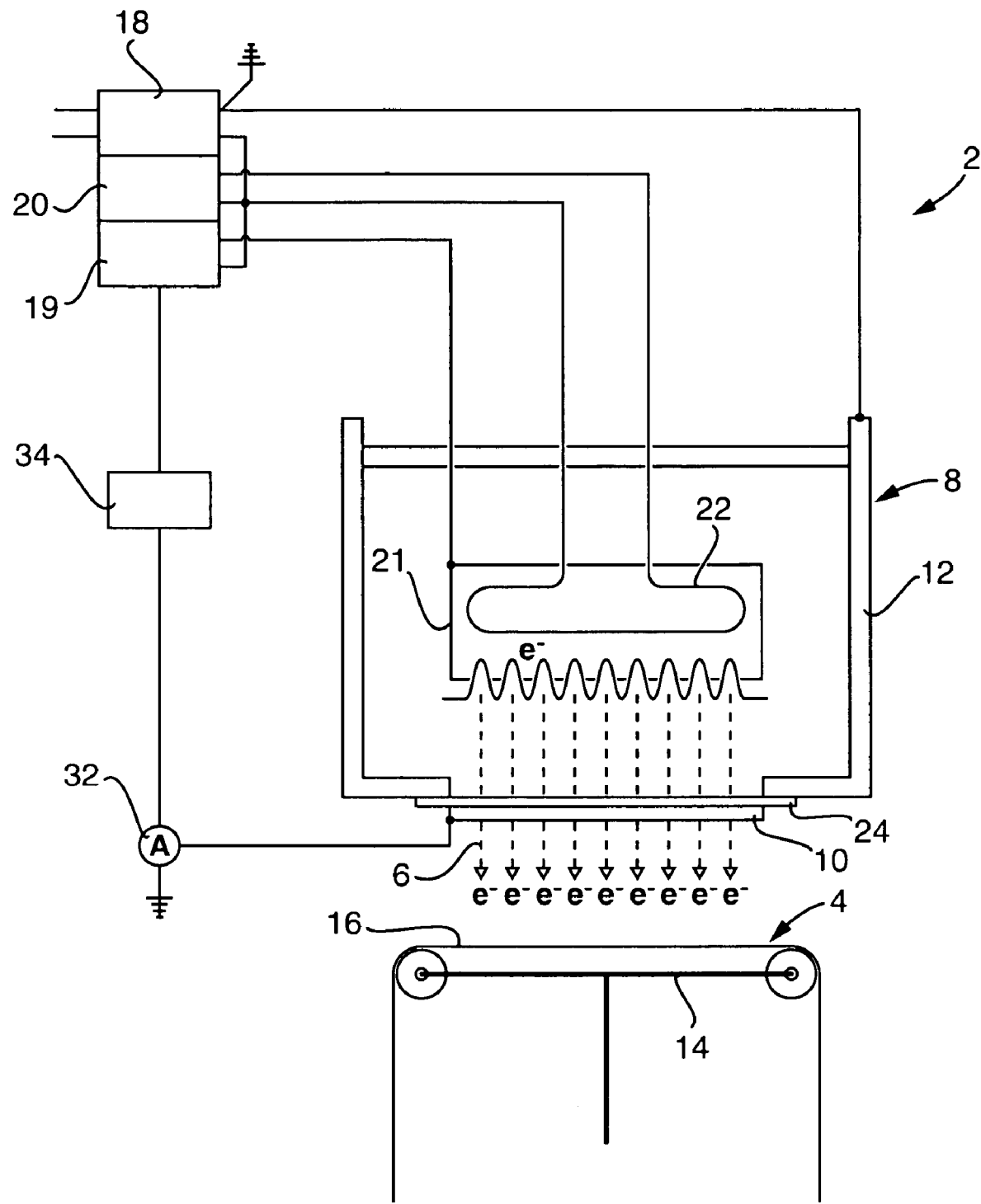
FIG. 1 schematically shows an exemplary system for irradiating a target in the form of a web with an electron beam, FIG. 2 schematically shows a cross section of an embodiment of a sensor according to the invention, FIG. 3 schematically shows a multisensor configuration of the invention, FIG. 4A-4B schematicaly show other multisensor configurations, and FIG. 5 schematically shows an exemplary system similar to that in FIG. 1 but for irradiating a target in the form of a ready-to-fill package.

FIG. 1 shows an exemplary system 2 for irradiating a target area 4 within an electron beam 6 emitted along a path. The exemplary system 2 includes means for emitting, such as an electron beam generator 8, for emitting an electron beam 6 along a path. The system 2 also includes means, such as sensor 10, for detecting electron beams 6. Thus, the system 2 includes both an electron beam generator 8 and a sensor 10. The sensor 10 is provided for sensing an intensity of the electron beam 6 generated by the electron beam generator 8 along a path which irradiates the target area 4. The electron beam generator 8 includes a vacuum chamber 12. The electron beam sensor 10 is formed and located in a way to be able to detect and measure the intensity of the electron beam 6 exiting the vacuum chamber 12.

A support 14 is provided for supporting a target 16 within the target area 4. In the embodiment shown in FIG. 1 the target is a web of packaging material 16 and the support 14 for the target can, for example, be a web material transport roller or any other suitable device of a packaging machine. Further, the support 14 can be used to hold the target 16 in the target area 4 at a desired measuring position relative to the sensor 10 and the generator 8.

The electron beam generator 8, as shown in FIG. 1, includes a high voltage power supply 18, suitable for providing sufficient voltage to drive the electrical beam generator 8 for the desired application. The electron beam generator 8 also includes a filament power supply 20, which transforms power from the high voltage power supply 18 to a suitable input voltage for a filament 22 of the generator 8. In addition, the high voltage power supply includes a grid control 19 for controlling a grid 21.

The filament 22 can be housed in the vacuum chamber 12. In an exemplary embodiment, the vacuum chamber 12 can be hermetically sealed. In operation, electrons (e⁻) from the filament 22 are emitted along an electron beam path 6 in a direction towards the target area 4.

Further, the electron beam generator 8 is provided with an electron exit window 24. The exit window 24 is used for diffusing the electron beam 6 into a more uniform beam, and for focusing the electron beam towards the target area 4. The window 24 can be made of a metallic foil, such as for example titanium, and can have a thickness in the order of 4-12 µm. A supporting net formed of aluminium or copper supports the foil from inside of the electron beam generator.

Figure 2:
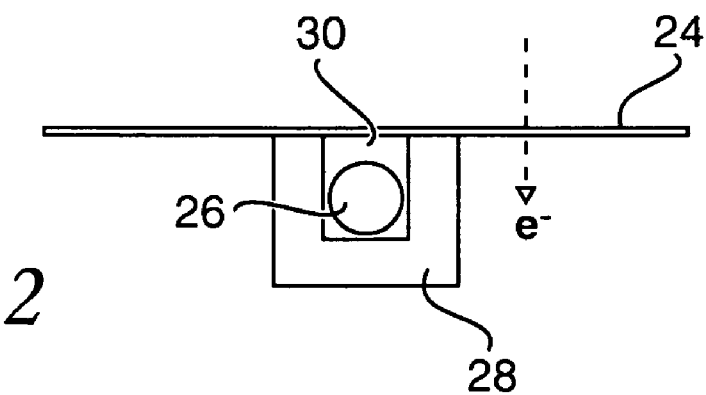

The sensor 10, of which an exemplary embodiment is shown in FIG. 2, comprises a conductor 26 formed as a bare wire probe or as composite of a core and an outer conductive layer. In an embodiment, the conductor 26 can be a cooper or stainless steel signal wire, or any other suitable conductor 26. For example, the outer conductive layer can be an inert conductive material, such as gold or gold plate. The thickness selected for the conductor 26 can be of any suitable dimension. For example, a relatively small conductor 26 can be used. In an exemplary embodiment, the diameter of the conductor 26 can be on the order of 0.3 millimeters (mm), or lesser or greater as desired. If sized of a suitably small dimension, the sensor 10 can be positioned within a direct path of the electron beam 6, between the filament 22 and the target area 4.

Further, the sensor 10 comprises an insulating housing 28 that can be made of any insulating material that can withstand temperatures in the order of a few houndred degrees Celsius (up to about 400 degrees Celsius). Examples of such materials are ceramic, titanium oxide and glass. The function of the insulating housing 28 is to shield the conductor 26 from plasma and secondary electrons. With the term "insulating" is meant that the housing 28 is electrically insulating, i.e. non-conductive.

Said housing 28 is engaged with the exit window 24 for forming a chamber 30 together with said exit window 24. The exit window 24 forms one wall of the chamber 30 and the insulating housing 28 forms the rest of the wall/s. In a presently preferred embodiment the housing 28 is U-shaped and the legs of the U-form are engaged to the window 24. Here, the term "engage" comprises every way the housing and the exit window can be related. They can be attached or fastened to each other in different ways, or they can be held or tightened against each other. The housing 28 is engaged with the window in such a way that it is engaged directly with the window surface, i.e. it is engaged with the foil.

The conductor 26 is positioned within said chamber 30. Preferably, the conductor 26 is not attached or in contact with the exit window 24, but bears on or is attached to the insulating housing 28. Of course, it would be possible to support the conductor 26 so that it can be spaced from insulating housing 28. However, it will still need to be spaced from the exit window 24 if the window surface is made of a conductive material.

The housing 28 can be sealed or attached to the surface of the exit window 24 by adhesive binding using for example an adhesive or glue used in high temperature applications, i.e. which can withstand the temperature near the exit window 24 during operation of the electron beam generator 8. The temperature is high, normally in the order of 300-400 degrees Celsius. An example of adhesive that can be used is organic glues.

The surface in contact with the surface of the exit window does not need to be fully glued. It may be possible to glue at certain isolated points on the contact surfaces.

In another embodiment of the invention the housing is held against and tightened to the surface of the exit window using supports in the end of the housing.

In this design the conductor 26 will be exposed to the electron beam 6. When introduced to the electron beam 6 the conductor 26 can capture electrons which can be recorded as an electrical current representing a momentary measure of the electron beam intensity. The conductor 26 can be configured of relatively small dimension to fit into any geometry. Typically, the conductor has a diameter in the order of 0.1-0.5 mm or even smaller. The diameter of the sensor will be in the order of 0.5-1.5 mm.

In the following, the term or concept of plasma or secondary electrons will be described. When an electron (e⁻) emitted from the filament 22 of FIG. 1 travels towards the target area 4, it will collide with air molecules along this path. The emitted electrons can have sufficient energy to ionize the gas along this path, thereby creating a plasma which contains ions and electrons. Plasma electrons are secondary electrons, or thermal electrons, with low energy compared to the electrons from the electron beam. The plasma electrons have randomised vector velocity and can only travel a distance which length is a small fraction of the mean free path for the beam electrons.

There will be a plasma inside the chamber 30 due to the presence of air in the chamber 30. However, the plasma there will be of a controlled, small size. Thus, it is possible to compensate for it in the measurements and calculations.

The chamber 30 is closed and fully encapsulates the conductor 26 at least within the electron beam path. The sensor 10 will extend along or across the exit window 24 and at the ends the housing 30 may be open to the environment. However, along the portion of the sensor 10 being exposed to the electron beam 6 it should preferably be closed to function as a proper plasma shield.

As already mentioned, electrons which reach the sensor 10 can be detected and measured. For example, a current detector 32 can be provided to detect electrical current in the conductor 26 of the sensor 10, as a measure of electron beam intensity. An output from the current detector 32 can be supplied to a controller 34, which in turn can serve as a means for adjusting the intensity of the electron beam 6 in response to an output of the sensor 10. In exemplary embodiments, the electron beam 6 can be emitted with an energy of, for example, less than 100 keV, e.g. 60 to 80 keV.

The current detector 32 can be any device suitable for measuring an intensity of the electron beam 6 either directly or indirectly. For example, the current detector 32 can be a voltmeter in combination with a resistor, or an ampere meter, or any other suitable device.

In an embodiment the sensor 10 comprises an array of conductors 26 with insulating housing 28 to detect an intensity of the electron beam at each of plural locations within the electron beam path 6. The sensor 10 can be said to comprise an array of sensors 10 in a grid arrangement or mesh of sensors attached to the exit window 24, see FIG. 3. Information from each conductor 26 (e.g., signal amplitudes, signal differences/ratios, conductor positions and so forth) can be used to produce an emission intensity plot via a processor 36. The grid arrangement also functions as a protection for the exit window 24 which is fragile.

Figure 3:
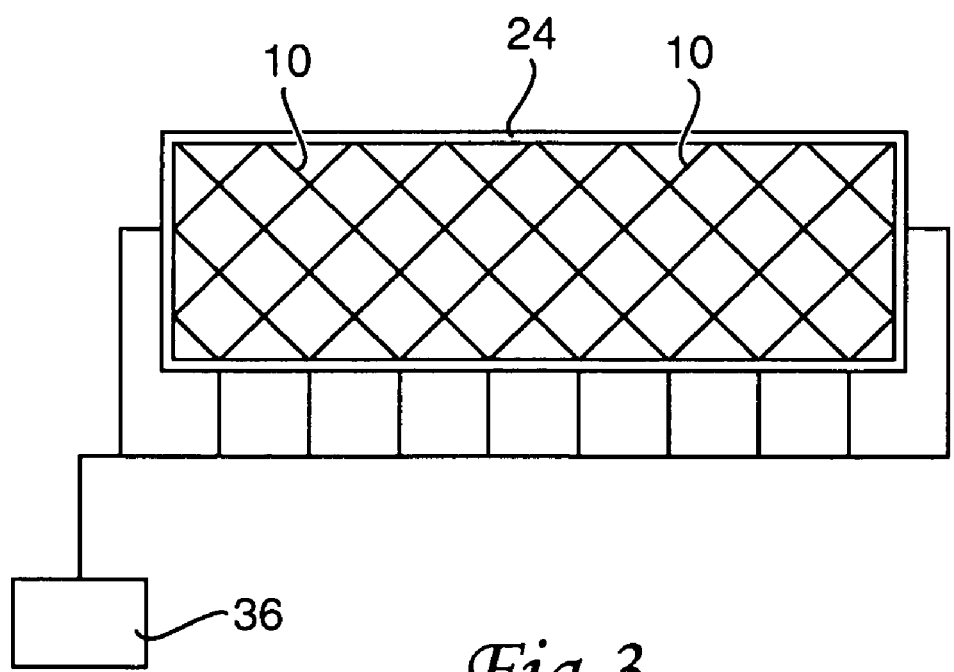

In addition, in the exemplary FIG. 3 embodiment, sensors 10 with its conductors 26 can be arranged at angles to one another, and/or at angles relative to a desired transport direction of the target 16 in the target area 4, and in a plane transverse to the electron beam path 6. Such a configuration can result in minimal shadowing of the target 16 passing beneath the grid. For example, where a target object, such as a packaging material web 16, passes from a lower portion of the diagram in FIG. 3 to a top of the diagram, all portions of the packaging material 16 will be irradiated by the electron beam 6 as the material passes. The angled sensors 10 will sense the electron beam at multiple locations across its two dimensional cross section, thereby providing an accurate plot of electron beam intensity without impacting the sterilization process.

Figure 4A:
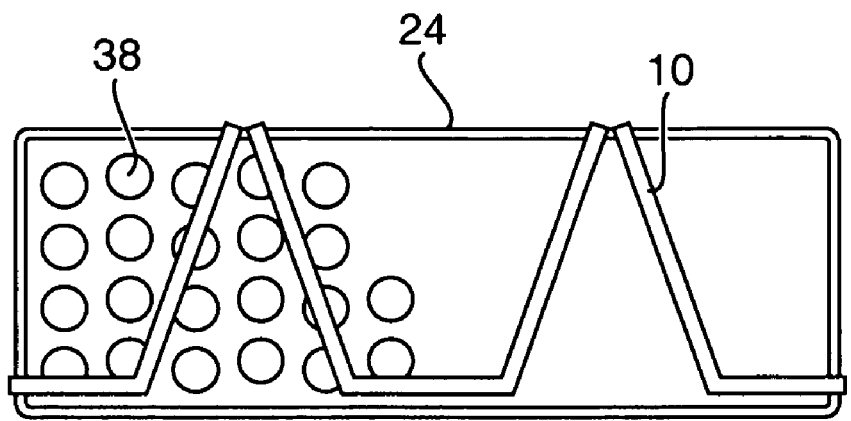
Figure 4B:
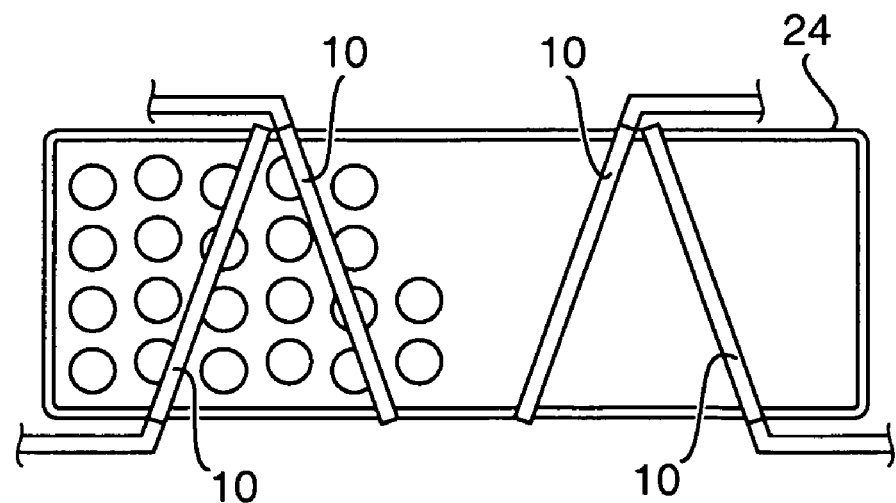

FIGS. 4A and 4B show exemplary embodiments of the electron beam exit window 24. The exit window 24 can be formed using a foil supported by an electron transparent structure. The holes 38 (of which only a few is drawn) of the supporting structure allow the electron beam 6 to pass from the vacuum chamber toward a sensor 10 in FIG. 4A. In FIG. 4B, multiple sensors are provided on the exit window 24 in a symmetrical arrangement. Any number of such sensors 10 can, of course, be used.

Figure 5:
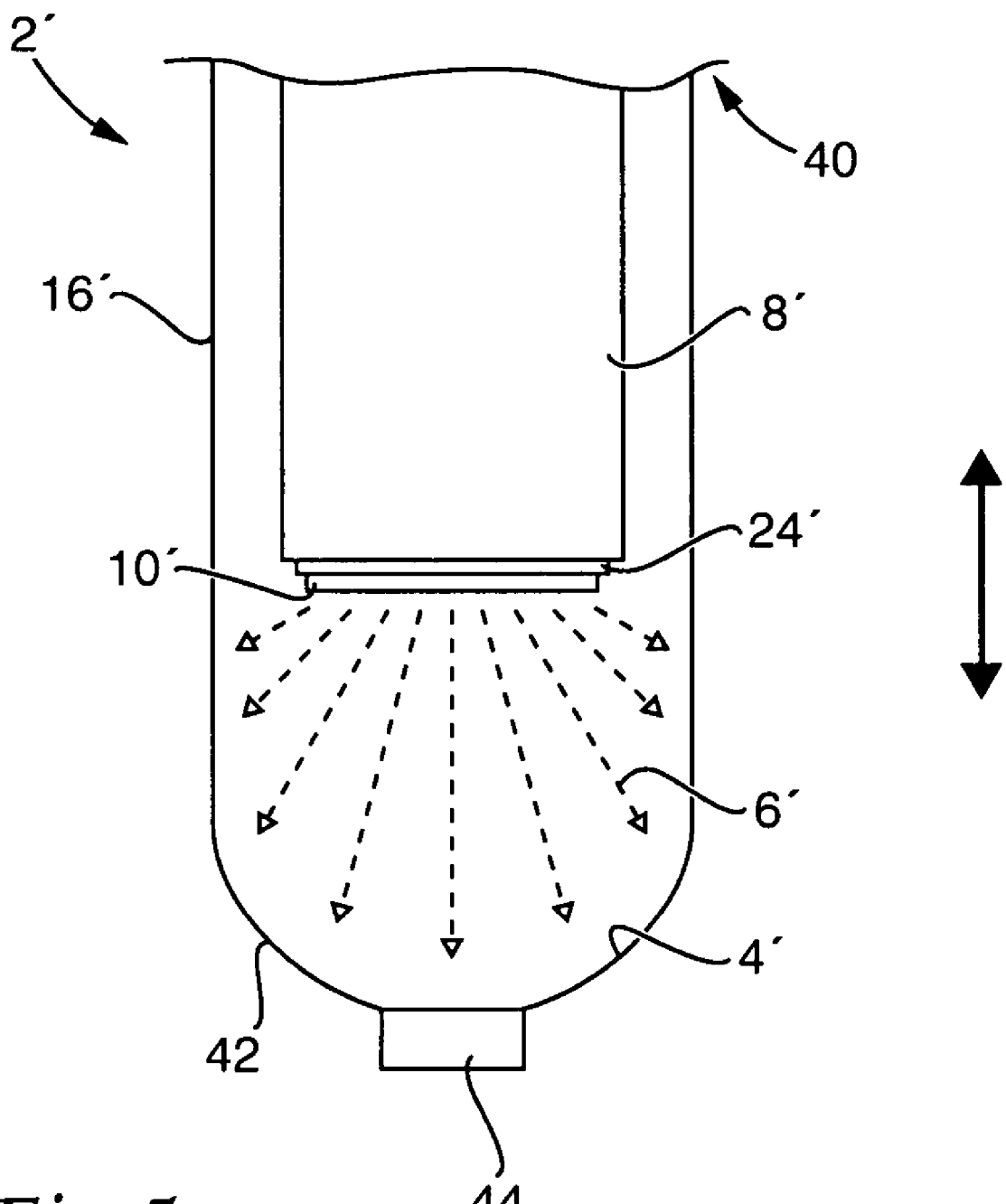

A sensor 10 like the one described may as well be used in connection with irradiation of targets 16 in the form of partly formed packages. Partly formed packages are normally open in one end and sealed to form a bottom or top in the other end and are commonly denoted Ready-To-Fill packages (RTF packages). In FIG. 5 a system 2' is schematically disclosed comprising an electron beam generator 8' for irradiation of a ready-to-fill package 16'. The package 16' is open it its bottom 40 and is provided in the other end with a top 42 and an opening device 44. During sterilization, the package 16' is placed upside down (i.e. the top 42 is located downwards) in a support (not shown). The support can be in the form of a carrier of a conveyor which transports the package 16' through a sterilization chamber. The system 2' comprises means (not shown) for providing a relative motion (see arrow) between the package 16' and the electron beam generator 8' for bringing them to a position in which said generator 8' is located at least partly in the package 16' for treating it. Either the generator 8' is lowered into the package 16', or the package 16' is raised to surround the generator 8', or each is moving towards each other. A sensor 10', for example being the sensor as described in FIG. 2, is adhered to an exit window 24' of the generator 8'.

Although the present invention has been described with respect to presently preferred embodiments, it is to be understood that various modifications and changes may be made without departing from the object and scope of the invention as defined in the appended claims.

For example it has been described that the housing 28 is adhered to the exit window 24 using an adhesive. It should be understood that the housing can be attached to the exit window in alternative ways, for example by bracing or welding.

A U-shaped housing 28 with a conductor wire 26 has been described. Other designs are of course possible as well. For example, the housing can be formed as a half-sphere. The conductor can have any other cross section such as rectangular, square-shaped or oval.

The invention claimed is:

1. A sensor for sensing an intensity of an electron beam generated by an electron beam generator along a path towards a target within a target area, the electron beam being exited from the generator through an exit window, wherein the sensor comprises a conductor located within the path and exposed to the exit window, and an insulating housing for shielding the conductor, said housing being engaged with the exit window forming a chamber with said window, and the conductor is positioned within said chamber.

2. Sensor according to claim 1, wherein the chamber is closed and fully encapsulates the conductor at least within the electron beam path.

3. Sensor according to claim 1, further comprising a current detector to detect electrical current in the conductor as a measure of electron beam intensity.

4. Sensor according to claim 1, wherein the insulating housing is adhered to the exit window using a high temperature resistant adhesive.

5. Sensor according to claim 1, wherein the insulating housing is held against and tightened to the exit window using supports in the end of the housing.

6. Sensor according to claim 1, wherein the conductor is in contact with the insulating housing, but prevented from being in contact with the exit window.

7. Sensor according to claim 1, wherein the conductor is formed with a core and an outer conductive coating.

8. Sensor according to claim 1, wherein the sensor comprises an array of conductors with insulating housings to detect an intensity of the electron beam at each of plural locations within the path.

9. Sensor according to claim 1, wherein the target is a package.

10. Sensor according to claim 1, wherein the target is a web of packaging material.

11. Sensor according to claim 10, wherein the sensor comprises an array of conductors with insulating housings to detect an intensity of the electron beam at each of plural locations within the path, and the conductors are arranged at angles relative to a desired transport direction of the web within the target area, and in a plane transverse to the path.

12. Sensor according to claim 1, wherein the target is a ready-to-fill package.

13. A system comprising:
an electron beam generator adapted to generate an electron beam along a path towards a target in a target area, the electron beam being exited from the generator through an exit window,
a sensor for sensing an intensity of the electron beam generated by the electron beam generator, the sensor being engaged with said exit window to detect and measure the electron beam intensity, the sensor including a conductor and an insulating housing shielding the conductor, wherein the housing engages the exit window to form a chamber with the exit window, and the conductor is positioned within the chamber, and
a support for supporting the target within the target area.

14. System according to claim 13, wherein the target is a web of packaging material.

15. System according to claim 14, wherein the support to hold the target in the target area comprises at least one packaging material web transport roller.

16. System according to claim 13, wherein the target is a package.

17. System according to claim 16, further comprising means for providing a relative motion between the package and the electron beam generator for bringing the package and the electron beam generator to a position in which said generator is located at least partly in the package for treating the package.

18. System according to claim 13, further comprising an electron beam controller to adjust the intensity of the electron beam in response to an output of the electron beam sensor.

19. System according to claim 13, further comprising a current detector to detect electrical current in the conductor of the sensor as a measure of electron beam intensity.

20. System according to claim 13, wherein the sensor comprises an array of conductors with insulating housings to detect an intensity of the electron beam at each of plural locations within the path.

* * * * *